United States Patent
Furstenberg et al.

(10) Patent No.: US 9,091,594 B2
(45) Date of Patent: Jul. 28, 2015

(54) CHEMICAL MAPPING USING THERMAL MICROSCOPY AT THE MICRO AND NANO SCALES

(71) Applicants: Robert Furstenberg, Burke, VA (US); Chris Kendziora, Burke, VA (US); Nabil D. Bassim, Silver Spring, MD (US); Robert Andrew McGill, Lorton, VA (US); Viet K. Nguyen, Gaithersburg, MD (US)

(72) Inventors: Robert Furstenberg, Burke, VA (US); Chris Kendziora, Burke, VA (US); Nabil D. Bassim, Silver Spring, MD (US); Robert Andrew McGill, Lorton, VA (US); Viet K. Nguyen, Gaithersburg, MD (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 5 days.

(21) Appl. No.: 13/684,535

(22) Filed: Nov. 25, 2012

(65) Prior Publication Data

US 2013/0134310 A1    May 30, 2013

Related U.S. Application Data

(60) Provisional application No. 61/563,665, filed on Nov. 25, 2011.

(51) Int. Cl.
  *G01J 5/02*    (2006.01)
  *G01J 3/28*    (2006.01)
  *G01J 3/02*    (2006.01)
  *G01J 5/60*    (2006.01)
  (Continued)

(52) U.S. Cl.
  CPC .............. *G01J 3/2823* (2013.01); *G01J 3/02* (2013.01); *G01J 5/60* (2013.01); *G01N 21/171* (2013.01); *G02B 21/008* (2013.01); *G02B 21/0028* (2013.01); *G01N 21/3563* (2013.01); *G01N 21/41* (2013.01); *G01N 21/45* (2013.01); *G01N 2021/1714* (2013.01); *G01N 2021/1725* (2013.01); *G01N 2021/1731* (2013.01); *G01N 2021/393* (2013.01)

(58) Field of Classification Search
  CPC .... G01N 29/72; G01N 29/228; G01N 29/348
  USPC ........................................... 250/341.6
  See application file for complete search history.

(56) References Cited

U.S. PATENT DOCUMENTS

| 4,733,175 | A  | * | 3/1988 | Levinson ................ 324/500 |
| 5,623,339 | A  | * | 4/1997 | Wickramasinghe et al. .. 356/501 |
| 6,840,671 | B2 | * | 1/2005 | Barron et al. ............ 374/130 |
| 6,917,423 | B2 |   | 7/2005 | Gardner, Jr. et al. |
| 8,101,915 | B2 |   | 1/2012 | McGill et al. |
| 8,222,604 | B2 |   | 7/2012 | McGill et al. |

(Continued)

OTHER PUBLICATIONS

Furstenberg et al., "Stand-off detection of trace explosives via resonant infrared photothermal imaging," Applied Physics Letters 93, 224103 (2008).

*Primary Examiner* — David Porta
*Assistant Examiner* — Edwin Gunberg
(74) *Attorney, Agent, or Firm* — US Naval Research Laboratory; Rebecca L. Forman

(57) ABSTRACT

A non-destructive method for chemical imaging with ~1 nm to 10 μm spatial resolution (depending on the type of heat source) without sample preparation and in a non-contact manner. In one embodiment, a sample undergoes photo-thermal heating using an IR laser and the resulting increase in thermal emissions is measured with either an IR detector or a laser probe having a visible laser reflected from the sample. In another embodiment, the infrared laser is replaced with a focused electron or ion source while the thermal emission is collected in the same manner as with the infrared heating. The achievable spatial resolution of this embodiment is in the 1-50 nm range.

24 Claims, 11 Drawing Sheets

(51) Int. Cl.

*G02B 21/00* (2006.01)
*G01N 21/17* (2006.01)
*G01N 21/3563* (2014.01)
*G01N 21/41* (2006.01)
*G01N 21/45* (2006.01)
*G01N 21/39* (2006.01)

(56) References Cited

U.S. PATENT DOCUMENTS

| | | |
|---|---|---|
| 8,421,017 B2 | 4/2013 | McGill et al. |
| 2002/0093354 A1* | 7/2002 | Enachescu et al. ........... 324/760 |
| 2005/0205779 A1* | 9/2005 | Falk .............................. 250/311 |
| 2010/0044570 A1* | 2/2010 | McGill et al. ............... 250/338.5 |
| 2011/0248166 A1 | 10/2011 | Diem et al. |

* cited by examiner

CHEMICAL MAPPING USING THERMAL MICROSCOPY AT THE MICRO AND NANO SCALES

PRIORITY CLAIM

This Application claims priority from U.S. Provisional Application No. 61/563,665 filed on Nov. 25, 2011 by Robert Furstenberg et al., entitled "Method of Chemical Imaging Using a Novel Confocal Photo-Thermal Microscopy Technique," the entire contents of which are incorporated herein by reference.

BACKGROUND OF THE INVENTION

1. Field of the Invention

The present invention relates generally to chemical imaging and, more specifically, to microscopic and nanoscopic photo-thermal chemical imaging.

2. Description of the Prior Art

With the increasing materials complexity of microfabricated devices, there is a growing need for new characterization techniques that provide chemical composition with improved spatial resolution over relevant scales. Existing established techniques are not always well suited for the length scales involved in microfabricated devices. For example, FTIR spectroscopy provides averaged chemical composition information for millimeter sized samples but without spatial information. While FTIR micro-spectroscopy addresses this problem, the practical resolution limit is limited to about 20 µm. X-ray mapping can achieve higher resolution but provides elemental maps, though this is not very useful for identification of organic compounds. On the other hand, well-developed imaging techniques with nanometer resolution capability (e.g. SPM, AFM, TEM/EELS) are often impractical to operate at the micron-scale. These techniques, operated at the nanometer scale, typically offer a limited physical footprint scan range, operate well with samples exhibiting only a limited range of surface roughness, and routinely require sample preparation.

The emerging technique of Raman micro-spectroscopy provides adequate spatial resolution (~1 µm). However, the process is inefficient and the signal response levels are extremely low, necessitating long integration times at each point, leading to long scan times and necessitating the use of expensive high performance detectors. In addition, samples which fluoresce cannot be practically characterized with Raman imaging.

The commercial techniques of combining atomic force microscopy and the photo-thermal effect provides chemical imaging with a spatial resolution as low as 0.1 µm. However, specialized sample preparation is needed, typically microtoming a sample to about 10 µm thin. Additionally, physical contact with both sides of the sample is required by a prism substrate and the scanning probe tip.

Photo-thermal spectroscopy (PTS) involves periodic heating of the sample and monitoring its response using either an IR detector or a visible probe beam (usually a HeNe laser). Photo-thermal IR imaging spectroscopy (PT-IRIS) for detection of chemicals at a distance has been implemented. In PT-IRIS, quantum cascade lasers (QCLs) are used to heat the sample and a long-wave IR detector is used as the imager. By varying the wavelength of the heating source across characteristic absorption bands the chemical composition of the sample is mapped out. However, the spatial resolution of this technique is diffraction limited by the long wavelength of the heating source and the thermal emission.

What is needed but not present in the prior art is a technique applicable to a wide range of samples, capable of mapping the chemical (molecular) information of the sample with spatial resolution better than 10 microns, and that is non-contact, non-destructive and requires limited or no sample preparation. The present invention satisfies all these criteria.

BRIEF SUMMARY OF THE INVENTION

The present invention provides a non-destructive method for chemical imaging with better than 10 µm spatial resolution without a requirement for sample preparation and examines the sample in a non-contact manner. In one embodiment, a sample undergoes photo-thermal heating using an IR laser and the resulting increase in thermal emissions is measured with either an IR detector or a laser probe having a visible laser reflected from the sample. In another embodiment, the infrared laser is replaced with a focused electron or ion source while the thermal emission is collected in the same manner as with the infrared heating. The achievable spatial resolution of this embodiment is in the 1-50 nm range.

In one approach, a sample undergoes photo-thermal heating using an IR laser and the resulting increase in thermal emissions is measured with either an IR detector or a laser probe having a visible laser reflected from the sample resulting in spatial resolution from 1 to 10 microns. The photo-thermal heating source is one that will provide emission signatures. Many applications for chemical imaging require a resolution between 1 and 10 µm including: characterization of MEMS and other microfabricated structures, heterogeneous materials (e.g. polymer blends), forensics (fingerprints, blood stains, residue from illicit drugs or explosives, etc.), pharmaceutical industry (identifying counterfeit pharmaceuticals), biological samples (e.g., cancerous tissue or cells, cataracts, etc.).

In another approach, focused electron or ion beams are used instead of infrared lasers to further decrease the size of the heated spot. This way, spatial resolutions well below 1 micron (to as low as 1 nm) are possible.

The purpose of the present invention is to provide a new non-contact and non-destructive imaging technique that eliminates the need for sample preparation and provides similar content information as FTIR or Raman spectroscopy (i.e. molecular information) while mitigating any fluorescence and luminescence effects, and offers rapid scan rates and/or higher spatial resolution. In one approach, it utilizes photo-thermal heating of the sample with a quantum cascade laser (or other suitable infrared laser) and measures the resulting increase in thermal emissions by either an infrared (IR) detector or a laser probe having a visible laser reflected from the sample. The latter case allows for further increases in the spatial resolution from ~10 µm to ~1 µm or better, with suitable experimental conditions. Since the thermal emission signal is proportional to the absorption coefficient at a given laser wavelength, by tuning the wavelength of the IR laser the IR absorption spectrum of the sample can be inferred from the thermal emission. By raster scanning over the surface of the sample, maps of the chemical composition of the sample surface can be obtained.

The IR absorption spectrum is the preferred spectral signature for identification of samples as it is much more independent of the form the sample is in. For example, it is well-known that particles have different scattering properties as a function of their size, especially if the size is comparable to the wavelengths of interest. This means that samples with substantial surface roughness or those that consist of small particulates will exhibit a change in spectral signatures, heavily influenced by scattering properties. Reflectance is such a spectral signature. The present invention overcomes this as the photo-thermal signal is proportional to the absorption spectrum. Nonetheless, this technique also allows one to simultaneously measure the reflectance spectrum along with absorption.

Along with the absorption spectrum in the wavelength range of the heating laser, additional molecular information about the sample is gained by spectrally resolving the thermal emission rather than just detecting the integrated signal. This is in accordance with Kirchhoff's Law which states that emission equals absorption in thermal equilibrium. Materials that provide a unique spectral signature in the wavelength range of a typical infrared detector will also offer a unique emission spectrum that is detected in the present invention. Most organic compounds fall in this category. For these, the present invention provides two unique wavelength ranges that can be used in identification. To be more specific, the thermal emission we detect is the product of the wavelength—(and to some degree temperature—) dependent emissivity function and the Planck's black body radiation function which is a smooth curve that starts from 0 at 0 wavelength and goes through a peak (its position determined by the temperature of the object) and back to zero at infinitely long wavelengths. For materials with approximately wavelength-independent emissivity (e.g. metals), the thermal emission is proportional to Planck's function and by spectrally resolving this spectrum, we can determine the absolute temperature of the object.

It is important to emphasize that the thermal emission is independent of the means of heating the sample. This means that both our laser based heat source and the electron and ion beam heat sources heat the sample and produce thermal radiation in a similar fashion that is monitored with infrared detectors. The main difference, produced by the different heating sources, is the lateral spot size and depth of the heating in the test sample.

The present invention has many advantages over current methods. There is potentially over an order of magnitude improvement in the spatial resolution compared to FTIR micro-spectroscopy. There is improved spatial resolution even without invoking the visible probe approach due to the use of coherent lasers. Simultaneous acquisition of confocal microscopy images is possible using the DC component of the visible probe. In addition to absorbance spectra, other thermal properties can be extracted from the data, such as thermal diffusivity. This setup can also collect polarization dependent reflectance spectra. Because the visible probe beam and infrared thermal emission use the same optical path, we need to use reflective optics which are inherently achromatic. A typical reflecting objective is of the Cassegrain design and has a numerical aperture of around 0.5. This is about half as much as possible with modern visible microscopy objectives. It is, however, conceivable that, at least in a limited range, a high-NA refractive objective that passes both visible and IR light could be used. For example, ZnSe has a limited transmittance for red light and it also spans the whole IR range. Other materials (e.g. MgF2, BaF2, CaF2 etc.) transmit visible light but have a IR cut-off in the 5-10 micron wavelength range. In both cases, the visible light probe would have to be converging or diverging compared to the IR beam to account for different focal lengths of the focusing objective at these disparate wavelengths.

These and other features and advantages of the invention, as well as the invention itself, will become better understood by reference to the following detailed description, appended claims, and accompanying drawings.

BRIEF DESCRIPTION OF THE DRAWINGS

FIG. 5a shows the optical image of the crystal, FIG. 5b shows the confocal microscope image. FIGS. 5c to 5e show images generated by the PT IR probe with the laser tuned to three different wavelengths: 6.10 µm, 6.13 µm, and 6.22 µm respectively.

FIG. 6a shows the sorbent polymer coated MEMS preconcentrator device that was imaged. FIG. 6b shows the FTIR plot for polyimide (bottom) and HCSFA2 (top). The polyimide membrane and the HCSFA2 sorbent coating are mapped in FIGS. 6c and 6d. FIGS. 6c and 6d are plotted using a false color scale where black represents low intensity and gray represents high intensity. The polyimide spectrum from an uncoated device is shown in FIG. 6e. FIG. 6f shows the PT spectrum on top of the platinum trace FIG. 6f. FIG. 6g shows the spectra of mixtures of polyimide and HCSFA2.

The magnitude of observed thermal emissions is inversely proportional to the local conductivity of the sample.

DETAILED DESCRIPTION OF THE INVENTION

Figure 1:
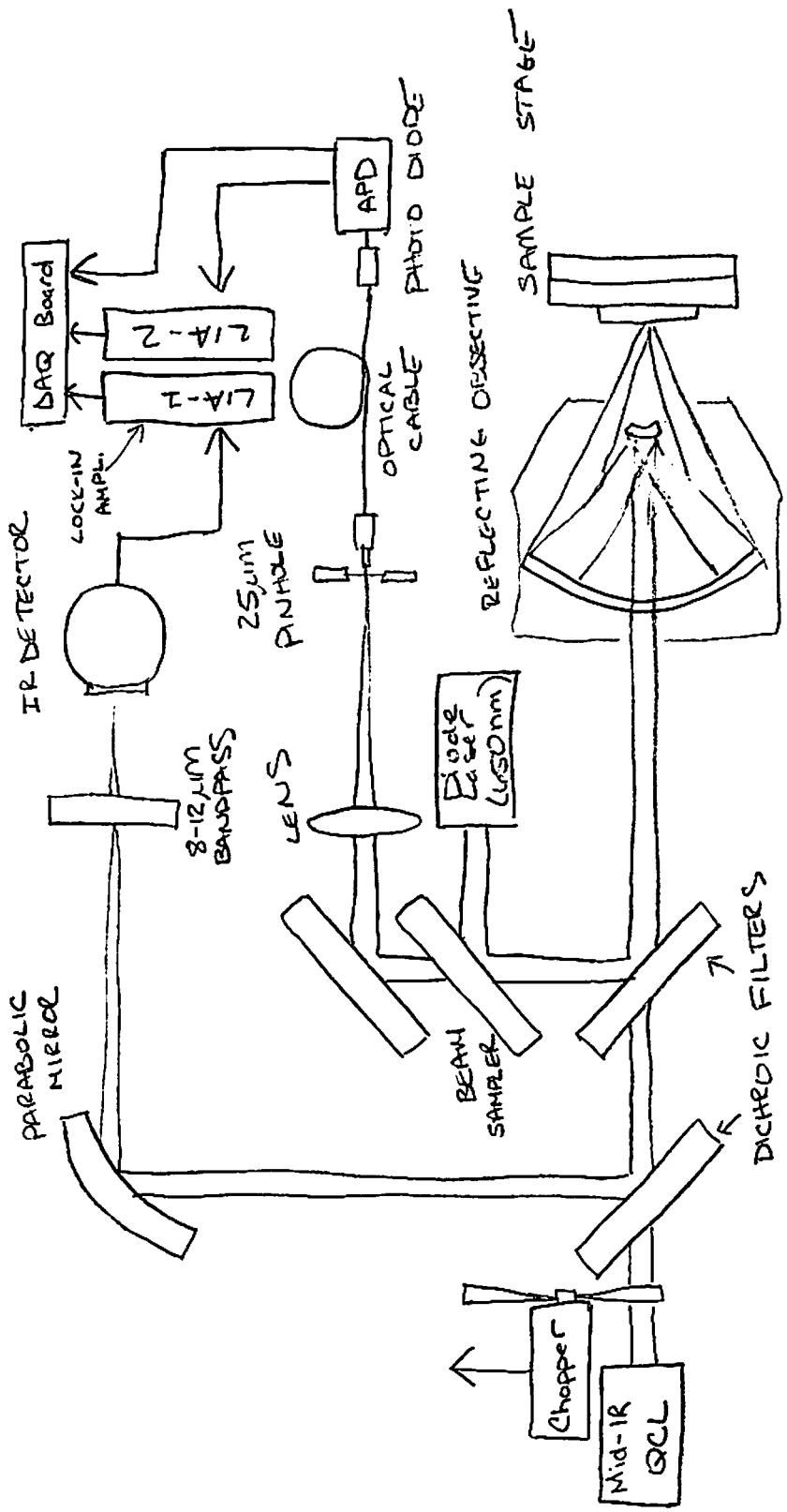
FIG. 1 is a schematic drawing of the photo-thermal confocal microscope.

One embodiment of the present invention uses a three-in-one instrument comprising a diffraction-limited PT microscope with an IR light detector, a sub-diffraction-limited PT microscope with visible light detector, and a standard confocal microscope (see FIG. 1). A sample undergoes photo-thermal heating using an IR laser and the resulting increase in thermal emissions is measured with either the IR detector or a laser probe having a visible laser reflected from the sample. The visible laser probe (operated in continuous wave (cw) mode) is co-focused with the IR beam at the sample. As the sample is periodically heated, the sample expands and contracts, with its surface moving up and down which modulates the reflected visible laser. The index of the refraction of the sample also changes and this is also registered as a change in reflectance. This modulation is demodulated by employing a lock-in detector.

Photo-Thermal Confocal Microscope

FIG. 1 shows the schematic drawing of the microscope. The infrared light from a QCL is combined with the output from a laser diode (~650 nm) using a dichroic filter. Both beams are focused on the sample using a reflecting objective (25×, 0.4 NA). The sample rests horizontally on a motorized stage. The visible light reflected from the sample is focused onto a multi-mode optical fiber (100 µm core size) that carries the light to an avalanche photo-diode. Since using a 100 µm core size may unnecessarily degrade the resolution, a 25 µm pinhole was placed before the fiber. The focusing of the laser beam on the sample is achieved by inserting a removable viewer in the beam path before the objective. The viewer is equipped with a beam splitter that directs the reflected beam to a camera.

The IR photo-thermal signal is collected with the same objective and focused onto a single channel IR detector (IR Associates, MCT-13-0.50), which has a 500 µm detector element. With this approach, the photo-thermal effect can be detected by two different probes (visible and IR). The IR laser is modulated (50% duty cycle) using a mechanical chopper. Both the visible probe and IR detector signals are demodulated using a digital lock-in amplifier. The DAQ board also collects the dc-component of the photo-diode signal as in a conventional confocal microscope. By removing the 8-12 µm bandpass filter, the setup can be converted to measure IR reflectance.

Spatial Resolution

Figure 2:
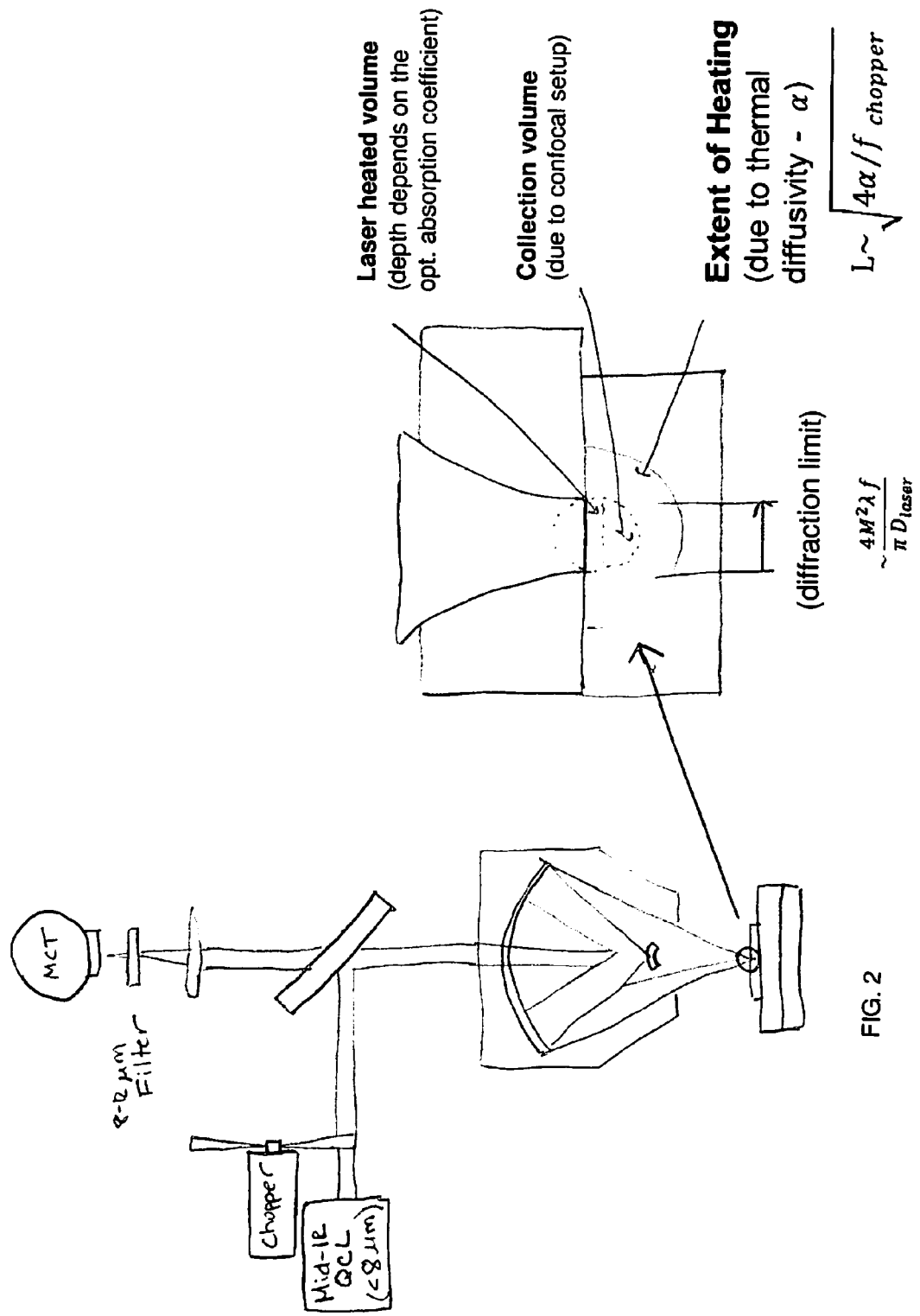
FIG. 2 is a schematic drawing of the diffraction-limited PT microscope.

FIG. 2 shows the schematic drawing of the diffraction-limited PT microscope. The spatial resolution of the IR detector probe is diffraction limited. Confocal geometry limits collection to a small volume, which minimizes thermal diffusion effects. The signal is proportional to the optical absorption coefficient, which is directly related to FTIR absorbance measurements. The theoretical laser spot size is given by $D_{spot}=4 M^2 \lambda f/\pi D_{laser}$. For the test-bed shown in FIG. 1 and for $\lambda=6.25$ µm, $M^2=1.3$ (manufacturer's claim), $D_{laser}=7$ mm (measured using a beam profiler) and $f=6.4$ mm, the laser spot is $D_{spot}=9.5$ µm. This approach has more optical excitation power than IR microscopy. Also, IR reflectance measurements are possible with the filter removed.

Figure 3:
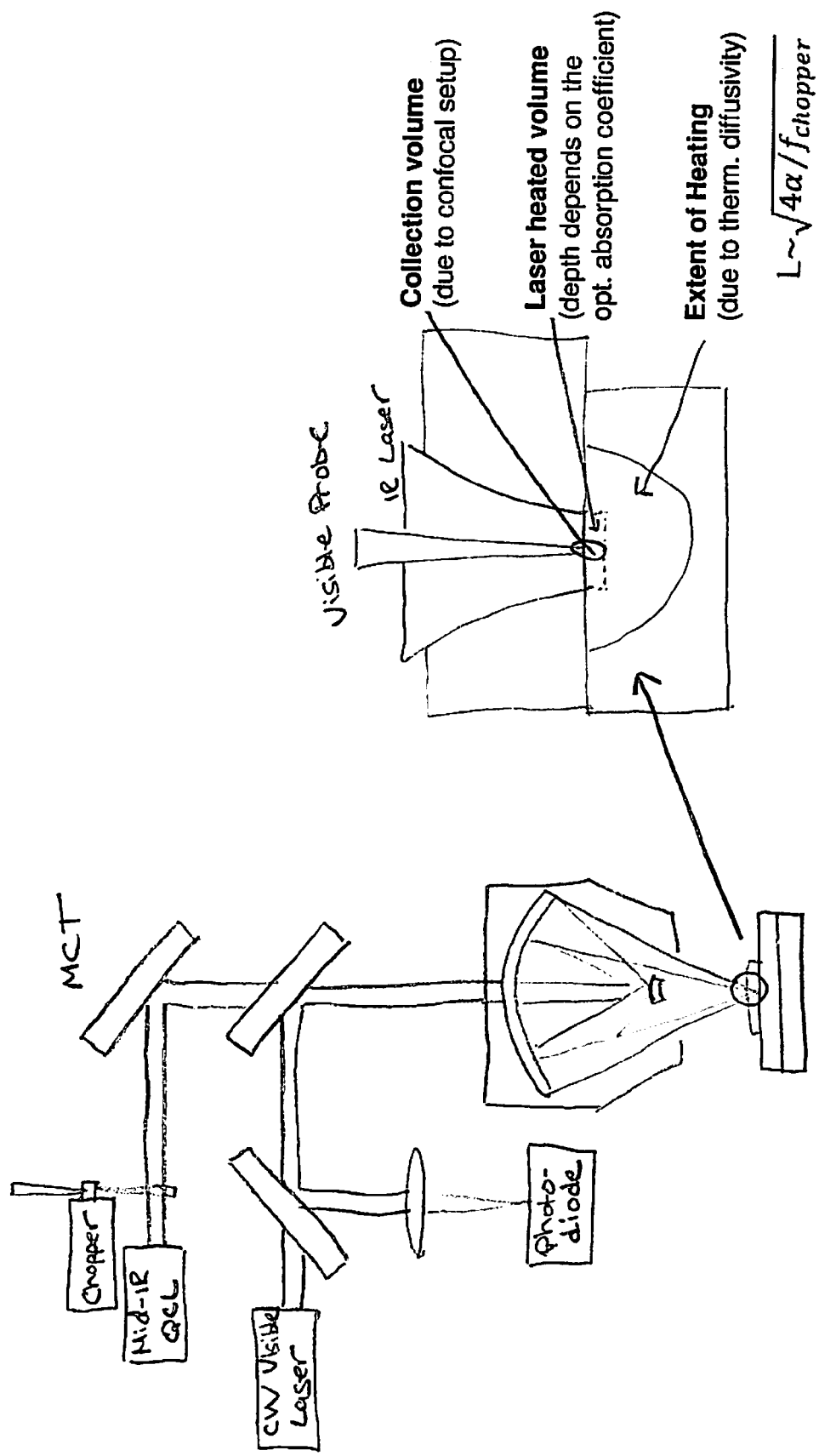
FIG. 3 is a schematic drawing of the sub-diffraction-limited PT microscope.

FIG. 3 shows the schematic drawing of the sub-diffraction-limited PT microscope. The ultimate spatial resolution is determined by the diffraction limit of the visible laser (<1 µm), not the IR excitation laser. The spatial resolution of the visible probe has an upper limit given by the diffraction limit of the visible light which, for a 0.4 NA objective, is slightly larger than the wavelength of light. This means that under certain conditions, photo-thermal microscopy can achieve 1 µm or even submicron resolution. For testing, the optics were chosen for a 1 µm limit, which is adequate given the use of a multimode laser diode that cannot focus to a smaller spot. PTS spatial resolution is driven by the thermal diffusivity of the sample. To take full advantage of the spatial resolution of the visible probe, the IR excitation laser needs to be modulated at a high enough frequency in order to limit thermal diffusion. This frequency is a function of not only sample diffusivity but also geometry. The worst-case value for the spatial resolution is given by $\sqrt{4\alpha/f}$, where $\alpha$ is the thermal diffusivity of the sample. This expression is derived for a one dimensional case. In our case, we have a point heat source. It was shown in the literature that when the heating is from a point source, the thermal diffusion effects are much smaller. Typically, a few kHz modulation is enough to restrict the thermal diffusion length to the size of the heating beam.

Test Samples

For testing, three different test samples were used:
1. A microscope calibration slide that provided a sharp transition region from a thin metallic coating to bare glass, which is useful in testing the spatial resolution of the microscope.
2. A crystal of 2,6-dinitrotoluene (DNT) on a glass slide. The sample was prepared by placing a crystal of DNT between two glass slides and applying pressure to crush the crystal into smaller sized crystals.
3. MEMS chemical vapor preconcentrator consisting of a thin perforated polyimide membrane supported by a silicon frame. The membrane had platinum meander-trace wires for heating and temperature sensing. Two versions were used: uncoated and one coated with a thin layer (0.9 µm) of a hydrogen-bond acidic hyperbranched carbosilane sorbent polymer (HCSFA2) used for selective adsorption of explosive vapors. A 5% solution of HCSFA2 in butanol was deposited on the device by an ink-jetting instrument (JetlabII by Microfab Inc.).

Spatial Resolution Test Using the Calibration Slide

Figure 4:
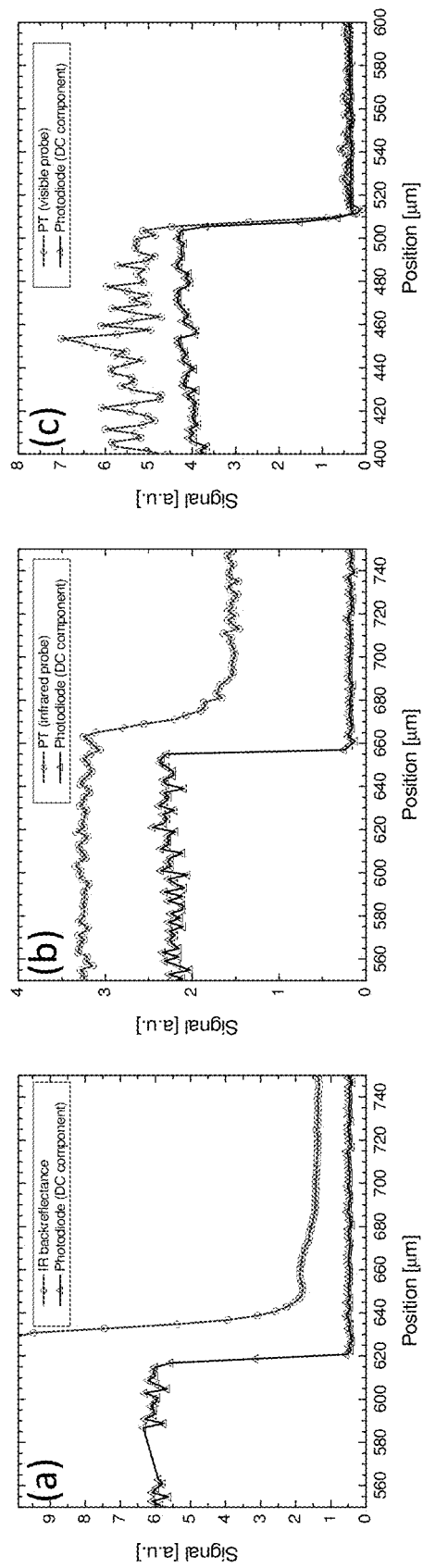
FIG. 4 shows line scans across a sharp metal/glass interface of a calibration slide. The bottom lines correspond to the dc component of the visible probe. The top lines correspond to the (a) IR back reflectance, (b) IR photo-thermal signal, and (c) visible PT probe signal.

To test the intrinsic spatial resolution of the visible probe, a line scan of the laser spot over the metal/glass edge was performed. The results are shown in dark lines in FIGS. 4a-c, and the spatial resolution is estimated to be 1-2 µm (in line with the 1 µm theoretical limit for the given test-bed). To test the resolution of the IR probe, the focused IR laser beam was scanned over the same edge and the reflected IR signal was monitored. FIG. 4b indicates that the resolution is approximately 10 µm.

It was also possible to observe the photo-thermal effect by using both probes. The result of the line scan for the IR probe is shown in FIG. 4b and for the visible probe in FIG. 4c. However, it should be pointed out that, due to large contrast in reflectance, this is not a suitable test sample to ascertain the spatial resolution for the photo-thermal probes. With this caveat, the resolution appears to be ~10 µm in FIG. 4b and 2 µm in FIG. 4c. Test samples studied in the next two subsections provide further clues about the spatial resolution of the microscope.

Chemical Imaging of a Small Crystal

To examine the chemical imaging capability of the PT microscope, a crystal of DNT on a glass slide was imaged. Both the DNT and glass absorb the IR laser and subsequently produce a photothermal response so this is a challenging test sample for imaging.

Figure 5:
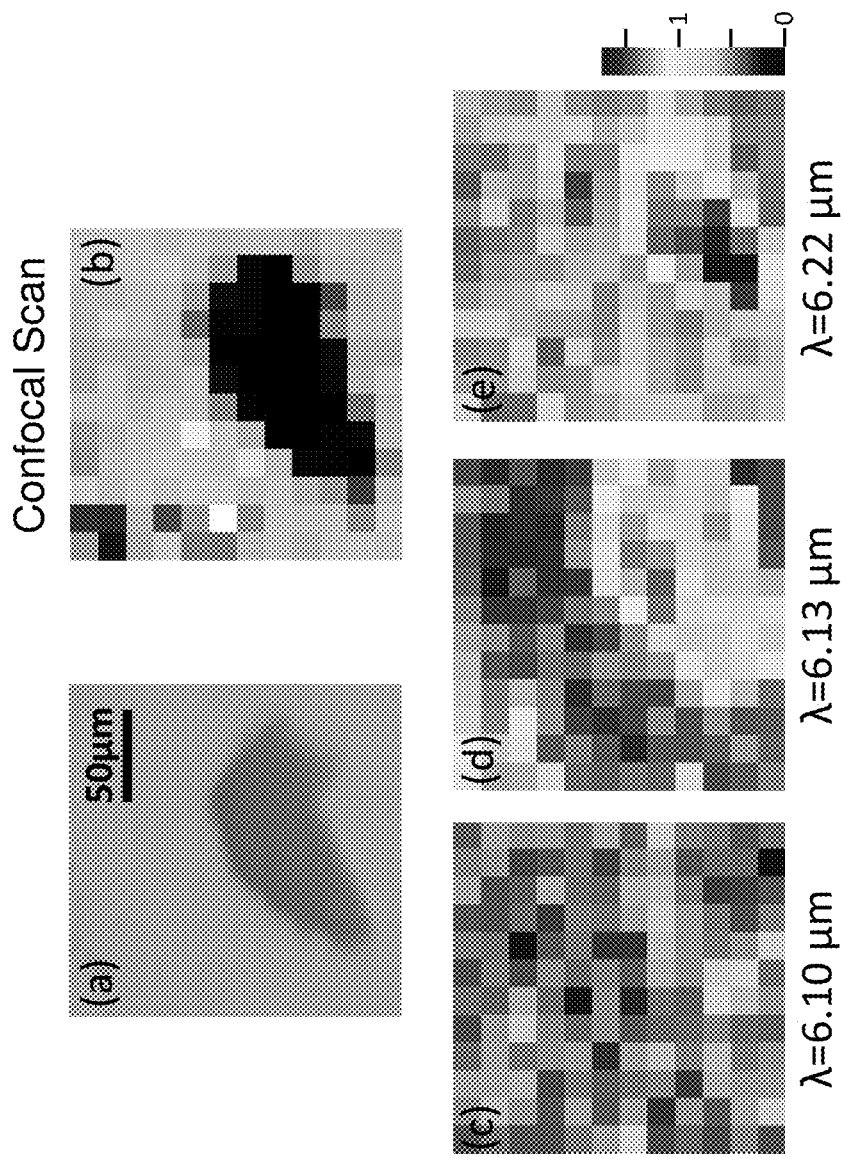
FIG. 5 shows photo-thermal imaging of a DNT crystal on glass.

The spatial raster scan consisted of 12 by 12 points with a 15 μm step size. The laser was tuned to 35 discrete wavelengths in the 6-6.6 μm spectral region. The raster scan was repeated for each wavelength. The dwell time at each point was ~300 ms, which was the minimum time required to move the stage between points. FIG. 5a shows the optical image of the crystal, while FIG. 5b shows the confocal microscope image. FIGS. 5c to 5e show images generated by the PT IR probe with the laser tuned to three different wavelengths. The wavelength in the last image (FIG. 5e) is near the absorption peak of DNT.

Due to the lack of flatness of the sample, only the photo-thermal signal for the IR probe was able to be observed, as the visible light probe has a significantly smaller depth of focus (~1 μm vs. ~10 μm for IR probe) and was defocused when on the crystal. The intensity of reflected light was below the noise level of the photo-diode. Another contributing factor was the lower amount of laser power (~4 mW) used to prevent the crystal from melting ($T_m$=66° C.).

Chemical Imaging of a MEMS Device

Figure 6:
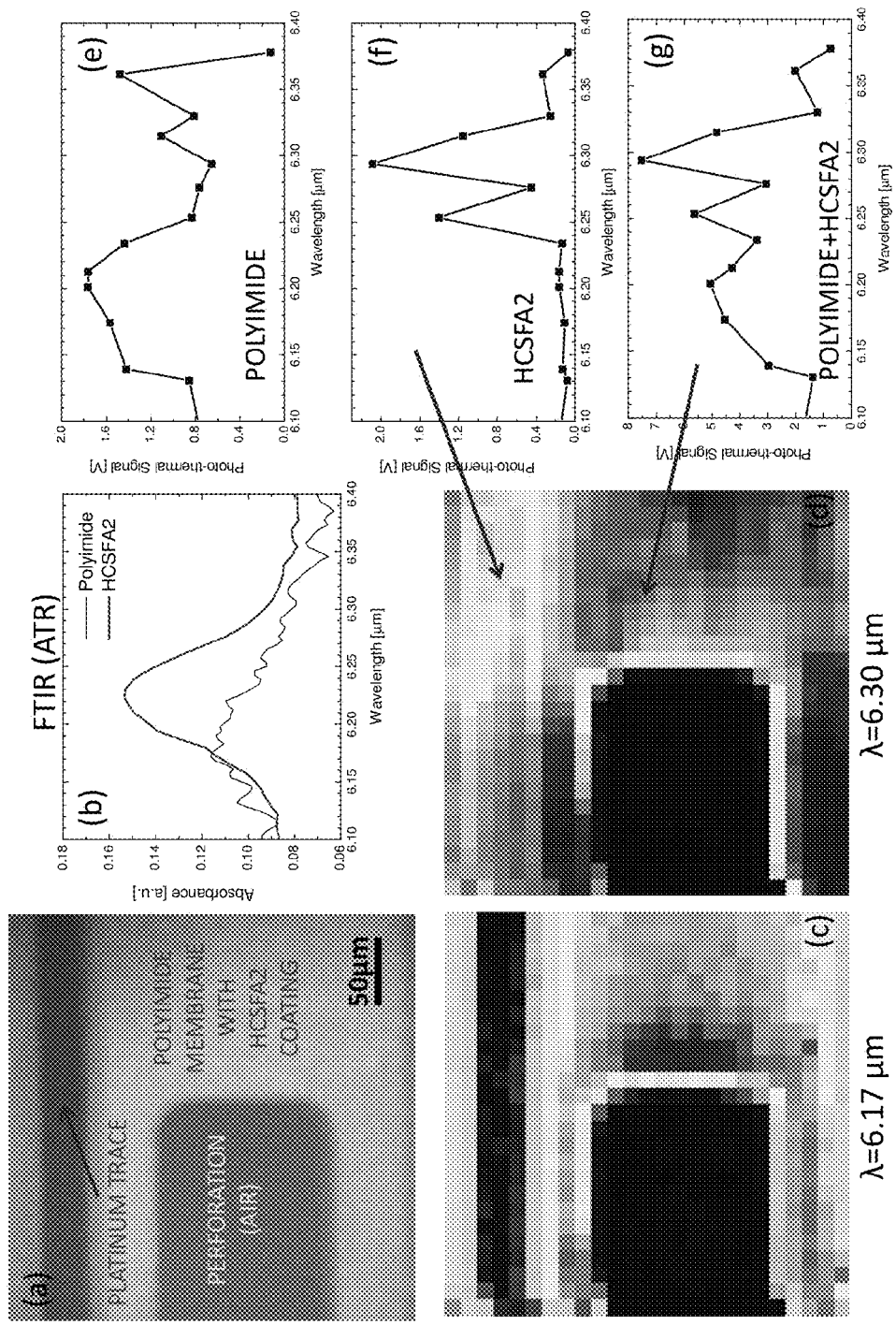
FIG. 6 shows chemical imaging of a MEMS preconcentrator coated with a sorbent polymer.

As a third test, the sorbent polymer coated MEMS preconcentrator device shown in FIG. 6a was imaged. The spatial raster scan consisted of 25 by 25 points with 12 μm steps. The laser was tuned to 14 discrete wavelengths in the 6-6.6 μm spectral region. FIG. 6b shows the FTIR plot for polyimide (bottom) and HCSFA2 polymer (top). The polyimide membrane and the HCSFA2 sorbent coating have absorption features that peak at 6.17 μm and 6.30 μm respectively, and are mapped in FIGS. 6c and 6d. FIGS. 6c and 6d are plotted using a false color scale where black represents low intensity and gray represents high intensity. The polyimide spectrum from an uncoated device is shown in FIG. 6e. The PT spectrum on top of the platinum trace (FIG. 6f) matches that of pure HCSFA2. In other parts of the device, the spectra are mixtures of polyimide and HCSFA2, as shown in FIG. 6g.

IR Nanoscopy

In order to further increase the spatial resolution of the sample, a focused electron or ion beam can be employed to heat a test sample. These beams are capable of focusing to spots on the order of a nanometer which is about 1000 times smaller than with the sub-diffraction limited photo-thermal setup described above. If the electron beam is modulated (5 kHz is sufficient—easily achievable with electrostatic blankers), the thermal diffusion is limited to the spatial resolution of the probe beam which then sets the overall spatial resolution of this nanoscopy technique. A limitation of this approach stems from the operation of the electron or ion beams in high vacuum chambers. In addition, sample preparation is often required. The main advantage over existing nanoscopy techniques is that it provides molecular information at the nanoscale, while examining a sample in a non-contact fashion and providing a path to increase the spatial resolution to <1 nm from 10 nm-100 nm claimed by AFM-(tip) based nanoscopy techniques. A non-contact approach is critical for measuring the inherent thermal properties on nanostructures, without the thermal contact interference from the probe tip. With sufficient signal strengths, the thermal emissions can be spectrally resolved to reveal infrared signatures of unique nanostructures. The thermal emissions can be collected by either a reflective optic (perhaps even with the same optic used in a cathodo-luminescence attachment), infrared lens (long focal length, positioned near a chamber port) or an infrared waveguide or optical fiber positioned in the vicinity of the sample that is then taken outside the chamber and re-imaged onto a detector. Alternatively, the detector (and even the preamplifier) can be positioned in the vicinity of the sample so a lens-less collection approach (fiber, waveguide) or a high NA, short focal length optic can be used to collect the thermal signal. This last approach is especially attractive if cooling of the detector and/or sample is possible.

Figure 7:
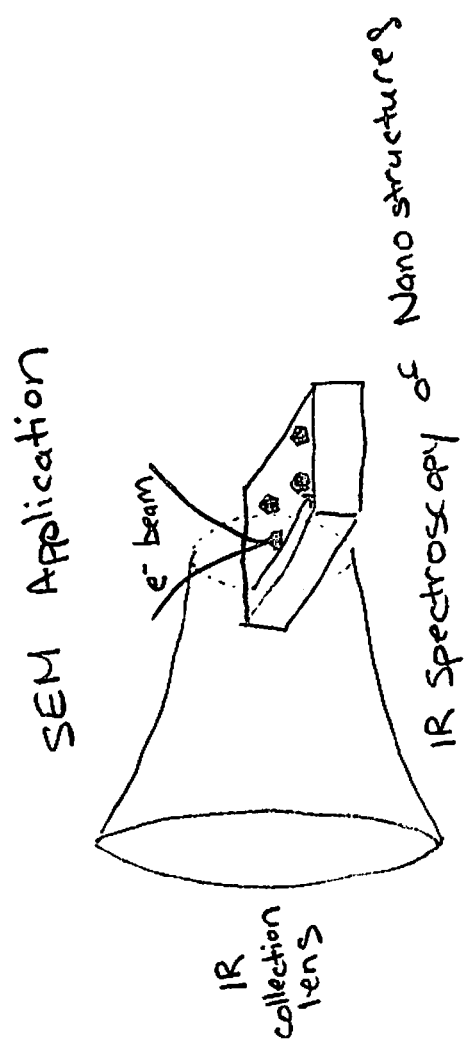
FIG. 7 shows the nanoscopy setup with an electron beam focused on the sample and the subsequent thermal emission collected with a lens or curved mirror. This thermal radiation is directed out of the vacuum chamber into a detector or spectrometer.

FIG. 7 shows the nanoscopy setup with an electron beam focused on the sample and the subsequent thermal emission collected with a lens or curved mirror. This thermal radiation is directed out of the vacuum chamber into a detector or spectrometer.

Figure 8:
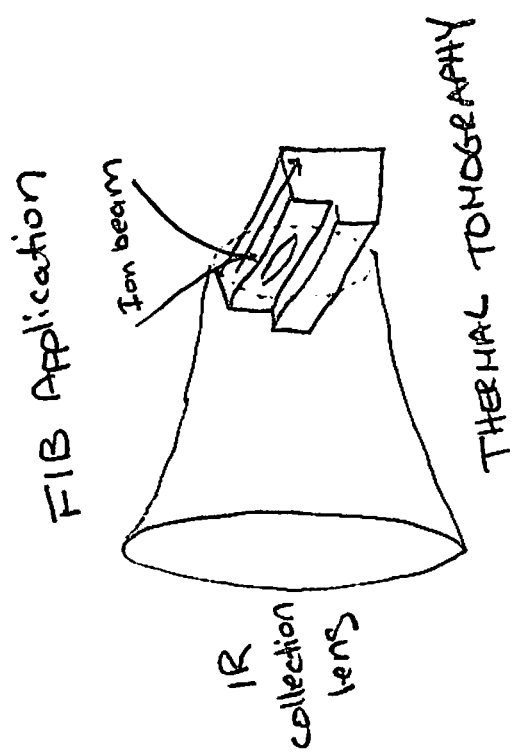
FIG. 8 shows the nanoscopy setup with an ion beam focused on the sample and the subsequent thermal emission collected with a lens or curved mirror. This thermal radiation is directed out of the vacuum chamber into a detector or spectrometer. As the ion beam mills the samples, deeper layers of the sample are heated and this way a 3D distribution of the thermal properties can be acquired.

FIG. 8 shows the nanoscopy setup with an ion beam focused on the sample and the subsequent thermal emission collected with a lens or curved mirror. This thermal radiation is directed out of the vacuum chamber into a detector or spectrometer. As the ion beam mills the samples, deeper layers of the sample are heated and this way a 3D distribution of the thermal properties can be acquired.

Figure 9:
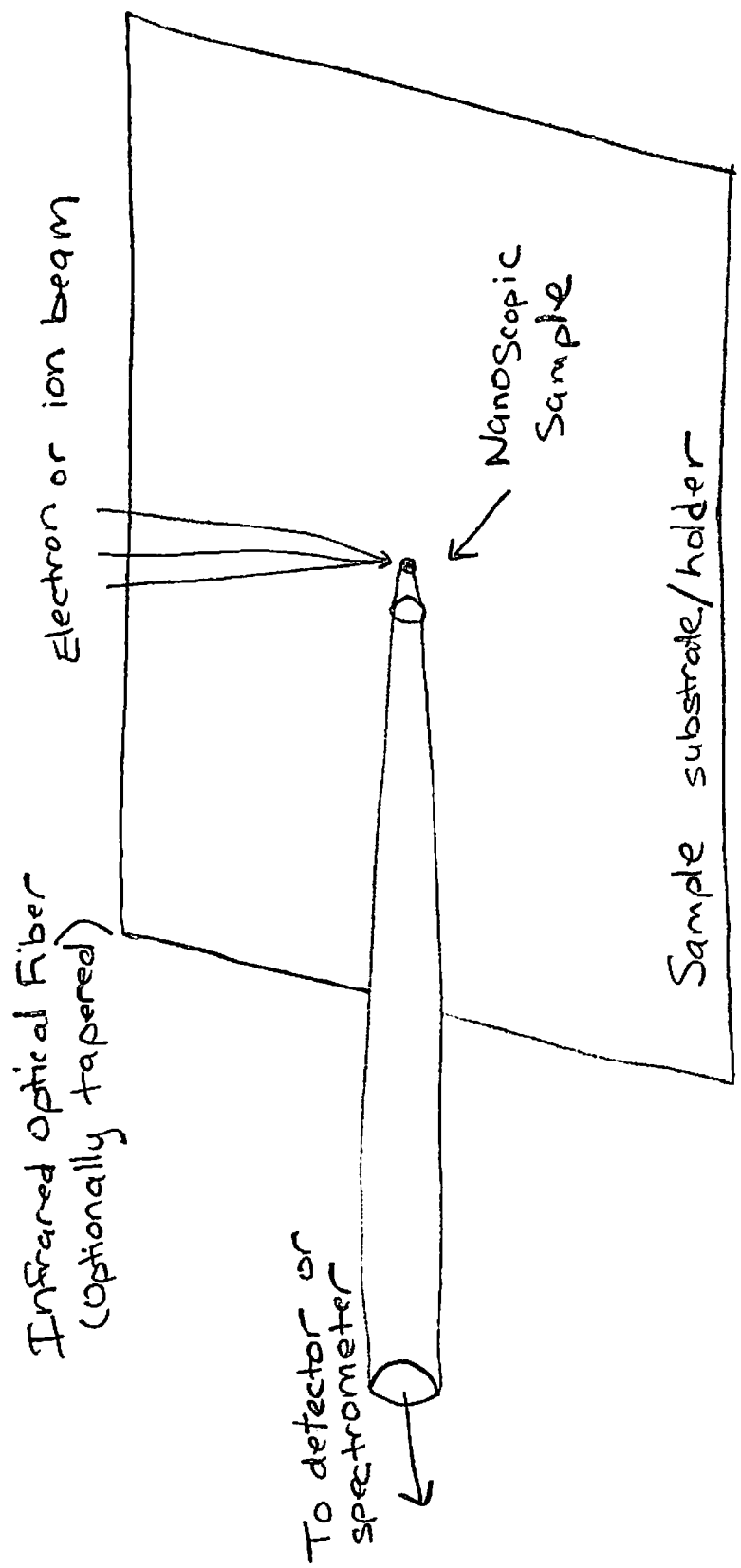
FIG. 9 shows an alternate light collection modality in which an optical fiber is in the direct vicinity of the sample. This arrangement is useful if the working distance of the electron microscope is limited. Also, by tapering the optical fiber and placing the sample at a distance less than the wavelength of thermal emissions, the area from which light enters the fiber is limited and therefore reduces stray background thermal radiation from around the samples or reflected from the ambient in case the substrate is reflective. This tapered fiber can optionally be a waveguide.

FIG. 9 shows an alternate light collection modality in which an optical fiber is in the direct vicinity of the sample. This arrangement is useful if the working distance of the electron microscope is limited. Also, by tapering the optical fiber and placing the sample at a distance less than the wavelength of thermal emissions, the area from which light enters the fiber is limited and therefore reduces stray background thermal radiation from around the samples or reflected from the ambient in case the substrate is reflective. This tapered fiber can optionally be a waveguide.

Figure 10:
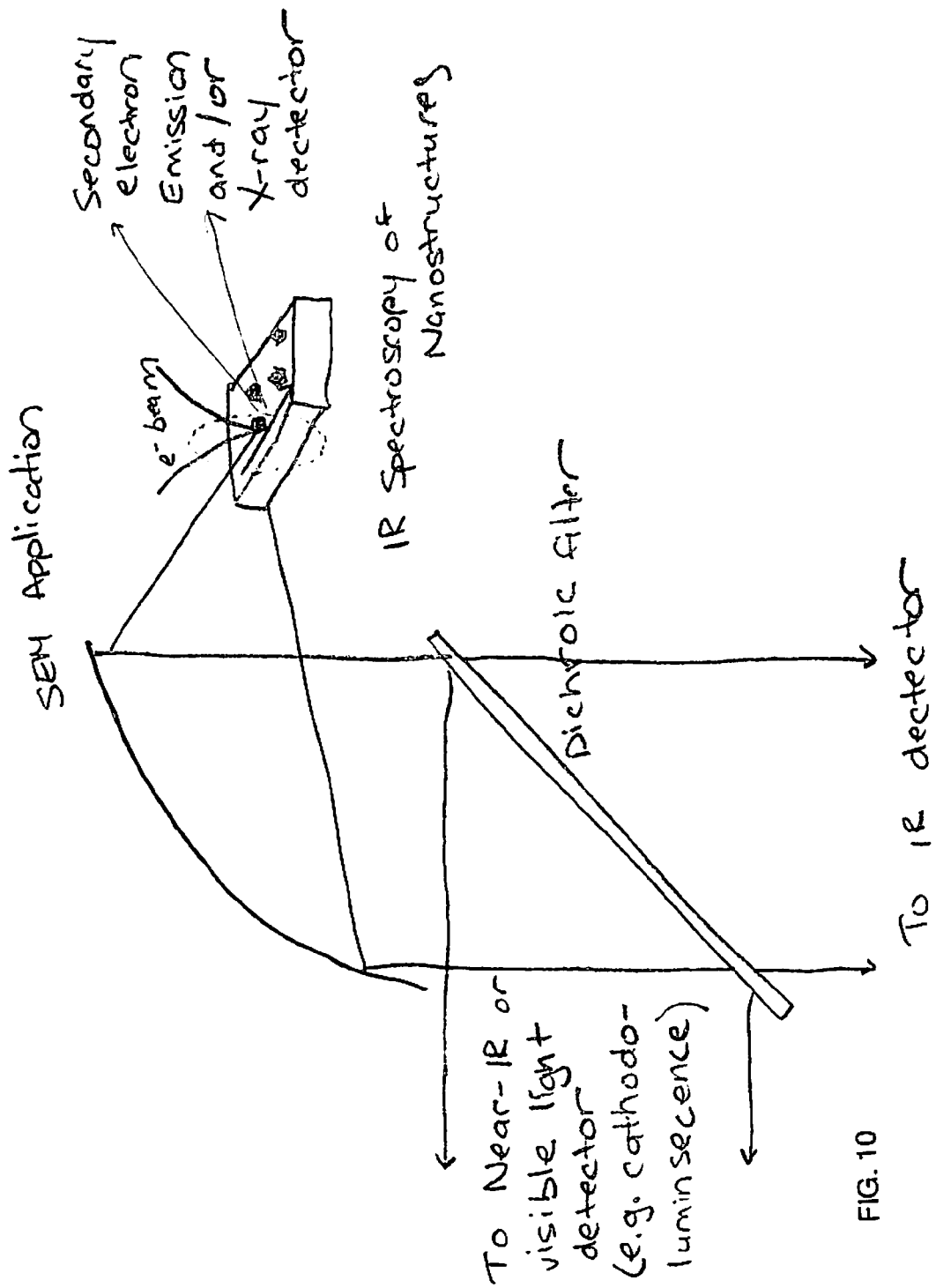
FIG. 10 shows an alternate collection geometry which allows for simultaneous collection of the (long-wave) infrared signal, short-wave IR, near-IR or visible light (e.g. cathodo-luminescence) and secondary electron emissions.

FIG. 10 shows an alternate collection geometry which allows for simultaneous collection of the (long-wave) infrared signal, short-wave IR, near-IR or visible light (e.g. cathodo-luminescence) and secondary electron emissions.

Electro-Thermal Microscopy

Electro-thermal spectroscopy is a modification to the photo-thermal setup to include active heating of the sample with electric current, instead of an infrared laser. This is useful for metallic and other conductive samples to map out the spatial distribution of the conductivity. Since the emissivity of metals does not change appreciably with wavelength, the two-wavelength technique (measuring the ratio of thermal emissions in two distinct wavelength regions) can be used to directly measure the temperature of the surface of the sample. By measuring the phase and magnitude of the signal and optionally varying the period of the heating pulses, one can map out the conductivity distribution from below the sample surface. The thermal signal can be measured by an infrared detector or the visible probe approach described in paragraphs above. If the infrared detector is used, it should detect at the shortest wavelength range at which there is available signal. The spatial resolution is directly proportional to the wavelength of detected light. Depending on the temperature of the sample, it may be possible to use short-wave or mid-wave infrared detectors.

Figure 11:
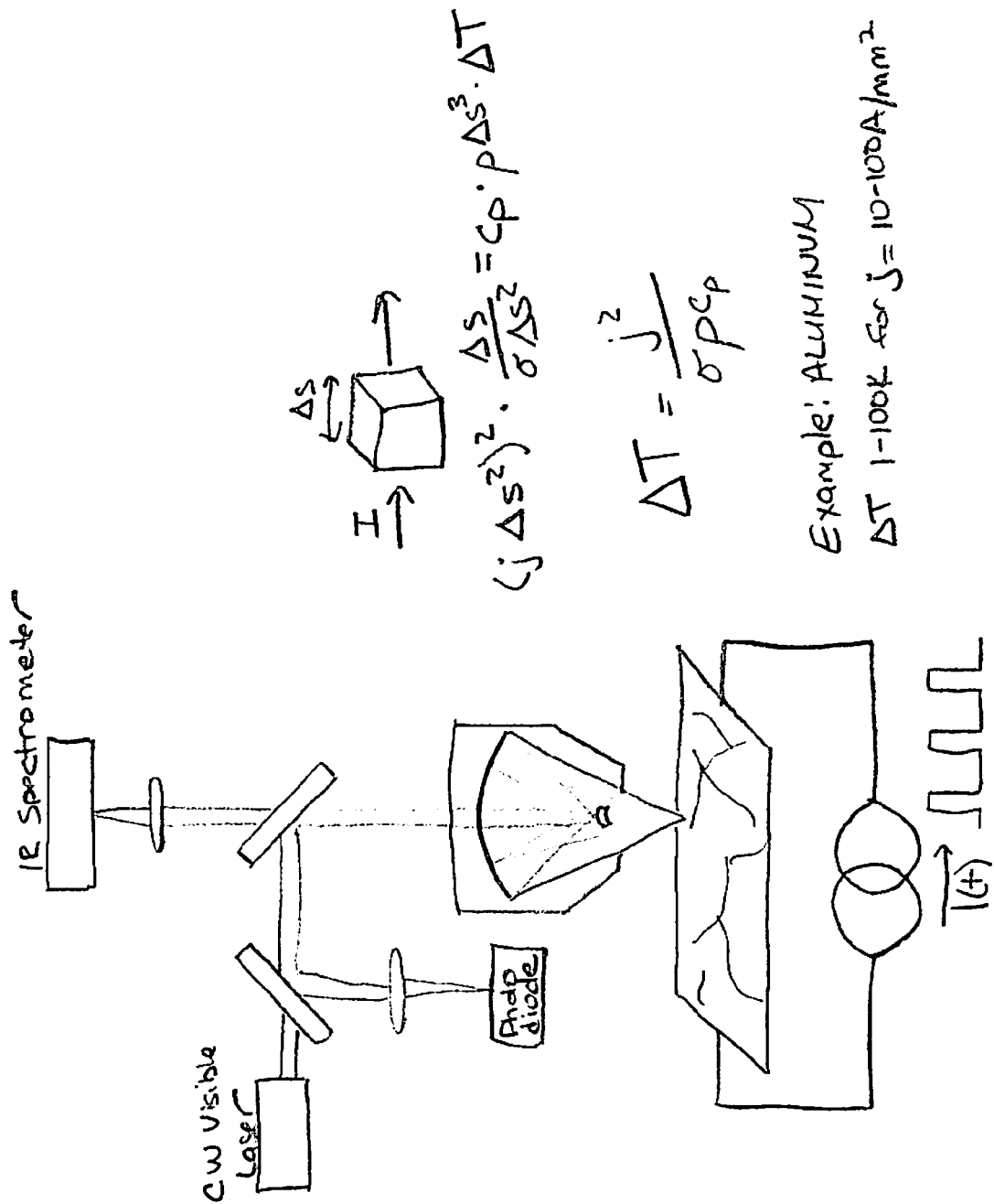
FIG. 11 shows the electro-thermal microscopy setup. The sample is fashioned into a thin strip (in order to maximize current density) and electrodes are attached to the ends of the sample. A dc or ac current is passed to the sample. If the current is ac, a lock-in detector is used to demodulate the amplitude of the heating signal at each point in the sample.

FIG. 11 shows the electro-thermal microscopy setup. The sample is fashioned into a thin strip (in order to maximize current density) and electrodes are attached to the ends of the sample. A dc or ac current is passed to the sample. If the current is ac, a lock-in detector is used to demodulate the amplitude of the heating signal at each point in the sample. The magnitude of observed thermal emissions is inversely proportional to the local conductivity of the sample.

The above descriptions are those of the preferred embodiments of the invention. Various modifications and variations are possible in light of the above teachings without departing from the spirit and broader aspects of the invention. It is therefore to be understood that the claimed invention may be practiced otherwise than as specifically described. Any references to claim elements in the singular, for example, using the articles "a," "an," "the," or "said," is not to be construed as limiting the element to the singular.

What is claimed as new and desired to be protected by Letters Patent of the United States is:

1. A method for photo-thermal spectroscopic imaging, comprising:
    using an infrared laser to photo-thermally heat a sample in a confocal setup and
    measuring the resulting increase in thermal emissions using a laser probe comprising an ultraviolet or visible laser reflected from the sample,
    wherein the method is non-contact, and
    wherein the sample is moved perpendicular to the surface of the sample to maximize the dc component of the visible probe which is used to reconstruct the topography of the sample.

2. The method of claim 1, wherein the infrared laser is tunable.

3. The method of claim 1, wherein the method does not require sample preparation.

4. The method of claim 1, wherein a bandpass filter is inserted before the infrared detector.

5. The method of claim 1, wherein the infrared signal is collected before, during and after the duration of the laser heating.

6. The method of claim 1, wherein the sample is scanned to construct images.

7. The method of claim 1, wherein the method has a spatial resolution of 1 µm or less.

8. The method of claim 1 wherein the heating laser power is modulated by either a mechanical chopper or electronic control.

9. A method for photo-thermal spectroscopic imaging, comprising:
    using an infrared laser to photo-thermally heat a sample in a confocal setup and
    measuring the resulting increase in thermal emissions using a laser probe comprising an ultraviolet or visible laser reflected from the sample,
    wherein the method is non-contact, and
    wherein the reflected signal from the visible probe is detected using an interferometry setup to maximize the weak signal due to small sample movement during heating.

10. The method of claim 9, wherein the infrared laser is tunable.

11. The method of claim 9, wherein the method does not require sample preparation.

12. The method of claim 9, wherein a bandpass filter is inserted before the infrared detector.

13. The method of claim 9, wherein the infrared signal is collected before, during and after the duration of the laser heating.

14. The method of claim 9, wherein the sample is scanned to construct images.

15. The method of claim 9, wherein the method has a spatial resolution of 1 µm or less.

16. The method of claim 9, wherein the heating laser power is modulated by either a mechanical chopper or electronic control.

17. A method for photo-thermal spectroscopic imaging, comprising:
    using an infrared laser to photo-thermally heat a sample in a confocal setup and
    measuring the resulting increase in thermal emissions using a laser probe comprising an ultraviolet or visible laser reflected from the sample,
    wherein the method is non-contact, and
    wherein the reflected signal from the visible probe is detected using an interferometry setup and wherein either a moving mirror arm of the interferometer or the sample are dithered at a higher frequency than the periodic heating to eliminate a varying photo-thermal signal.

18. The method of claim 17, wherein the infrared laser is tunable.

19. The method of claim 17, wherein the method does not require sample preparation.

20. The method of claim 17, wherein a bandpass filter is inserted before the infrared detector.

21. The method of claim 17, wherein the infrared signal is collected before, during and after the duration of the laser heating.

22. The method of claim 17, wherein the sample is scanned to construct images.

23. The method of claim 17, wherein the method has a spatial resolution of 1 µm or less.

24. The method of claim 17, wherein the heating laser power is modulated by either a mechanical chopper or electronic control.

* * * * *